(12) United States Patent
Shamay et al.

(10) Patent No.: US 11,229,446 B2
(45) Date of Patent: Jan. 25, 2022

(54) DEVICES FOR THE REMOVAL OF CLOTS

(71) Applicant: AMNIS THERAPEUTICS LTD., Or Akiva (IL)

(72) Inventors: Noam Shamay, Moshav Beit Uziel (IL); Ronen Ariel Plis, Or Akiva (IL); Evyatar Sirabella, Or Akiva (IL); Hadar Bukai, Or Akiva (IL); Maya Karnibad, Or Akiva (IL)

(73) Assignee: AMNIS THERAPEUTICS LTD., Or Akiva (IL)

( * ) Notice: Subject to any disclaimer, the term of this patent is extended or adjusted under 35 U.S.C. 154(b) by 229 days.

(21) Appl. No.: 16/617,868

(22) PCT Filed: May 31, 2018

(86) PCT No.: PCT/IL2018/050595
§ 371 (c)(1),
(2) Date: Nov. 27, 2019

(87) PCT Pub. No.: WO2018/220635
PCT Pub. Date: Dec. 6, 2018

(65) Prior Publication Data
US 2020/0085456 A1    Mar. 19, 2020

(30) Foreign Application Priority Data
Jun. 1, 2017    (IL) .......................................... 252608

(51) Int. Cl.
*A61B 17/221* (2006.01)
*A61F 2/01* (2006.01)
(Continued)

(52) U.S. Cl.
CPC ............ *A61B 17/221* (2013.01); *A61F 2/013* (2013.01); *A61B 2017/00004* (2013.01);
(Continued)

(58) Field of Classification Search
CPC ........... A61B 2017/22044; A61B 2017/00778; A61B 2017/00809; A61B 2017/00818;
(Continued)

(56) References Cited

U.S. PATENT DOCUMENTS 6,685,722 B1   2/2004   Rosenbluth et al.
7,766,921 B2   8/2010   Sepetka et al.
(Continued)

FOREIGN PATENT DOCUMENTS

CN     103547224 A    1/2014
CN     106413593 A    2/2017
(Continued)

OTHER PUBLICATIONS

Gory et al., "Histopathologic Evaluation of Arterial Wall Response to 5 Neurovascular Mechanical Thrombectomy Devices in a Swine Model", Am J Neuroradiol, 2013, vol. 34, pp. 2192-2198.
(Continued)

*Primary Examiner* — Wade Miles
(74) *Attorney, Agent, or Firm* — Vorys, Sater, Seymour and Pease LLP; William L. Klima

(57) ABSTRACT

Provided are medical devices, systems and methods for retrieval and/or extraction of a corpus located in a tubular organ. Systems of this disclosure are configured for carrying out various procedures for removal of occlusive corpus from tubular organs, for example thrombectomy.

20 Claims, 15 Drawing Sheets

(51) Int. Cl.
*A61B 17/00* (2006.01)
*A61B 17/22* (2006.01)
*A61B 90/00* (2016.01)

(52) U.S. Cl.
CPC ........... *A61B 2017/0088* (2013.01); *A61B 2017/00292* (2013.01); *A61B 2017/00778* (2013.01); *A61B 2017/00809* (2013.01); *A61B 2017/00818* (2013.01); *A61B 2017/00862* (2013.01); *A61B 2017/00867* (2013.01); *A61B 2017/00893* (2013.01); *A61B 2017/2212* (2013.01); *A61B 2017/22044* (2013.01); *A61B 2017/22051* (2013.01); *A61B 2090/3966* (2016.02)

(58) Field of Classification Search
CPC .. A61B 2017/320725; A61B 17/32075; A61B 17/221; A61B 2017/2212; A61B 17/22031; A61B 2017/22034; A61B 2017/22035; A61B 2/012; A61B 2/013; A61B 2/014; A61B 2002/015; A61M 2025/0024

See application file for complete search history.

(56) References Cited

U.S. PATENT DOCUMENTS

| | | | |
|---|---|---|---|
| 8,715,227 B2 | 5/2014 | Kontos | |
| 10,016,206 B1* | 7/2018 | Yang | A61B 17/221 |
| 2005/0004596 A1* | 1/2005 | McGuckin, Jr. | A61F 2/0108 |
| | | | 606/200 |
| 2005/0015111 A1* | 1/2005 | McGuckin, Jr. | A61F 2/0108 |
| | | | 606/200 |
| 2009/0171293 A1* | 7/2009 | Yang | A61M 25/04 |
| | | | 604/164.04 |
| 2010/0249815 A1* | 9/2010 | Jantzen | A61B 17/22031 |
| | | | 606/159 |
| 2010/0286722 A1* | 11/2010 | Rizk | A61F 2/0108 |
| | | | 606/200 |
| 2011/0184447 A1* | 7/2011 | Leibowitz | A61B 17/320016 |
| | | | 606/170 |
| 2011/0276081 A1* | 11/2011 | Kilemnik | A61F 2/94 |
| | | | 606/198 |
| 2012/0172973 A1* | 7/2012 | Deckard | A61B 17/12172 |
| | | | 623/1.16 |
| 2013/0035713 A1* | 2/2013 | Snow | A61F 2/0103 |
| | | | 606/200 |
| 2013/0116500 A1* | 5/2013 | Kohl | A61B 17/320725 |
| | | | 600/36 |
| 2014/0277013 A1* | 9/2014 | Sepetka | A61B 17/32075 |
| | | | 606/159 |
| 2015/0250497 A1 | 9/2015 | Marks et al. | |
| 2015/0305756 A1* | 10/2015 | Rosenbluth | A61B 17/221 |
| | | | 606/159 |
| 2016/0287283 A1* | 10/2016 | Vetter | A61B 17/320758 |

FOREIGN PATENT DOCUMENTS

| | | |
|---|---|---|
| CN | 106618676 A | 5/2017 |
| EP | 1 312 314 A1 | 5/2003 |
| WO | 2011/130256 A2 | 10/2011 |
| WO | 2013/054324 A1 | 4/2013 |
| WO | 2013/112944 A1 | 8/2013 |
| WO | 2014/141226 A1 | 9/2014 |
| WO | 2017/072761 A1 | 5/2017 |

OTHER PUBLICATIONS

Gralla et al., "A Dedicated Animal Model for Mechanical Thrombectomy in Acute Stroke", Am J Neuroradiol, 2006, vol. 27, pp. 1357-1361.

Grunwald et al., "Endovascular Stroke Treatment Today", Am J Neuroradiol, 2011, vol. 32, pp. 238-243.

Levy et al., "Self-Expanding Versus Balloon-Mounted Stents for Vessel Recanalization Following Embolic Occlusion in the Canine Model: Technical Feasibility Study", Am J Neuroradiol, 2006, vol. 27, pp. 2069-2072.

Mordasini et al., "Thrombectomy for Acute Ischemic Stroke Treatment: A Review", EJMINT Invited Review, 2012, 1238000077, 10 pages.

Nogueira et al., "Endovascular Approaches to Acute Stroke, Part 1: Drugs, Devices, and Data", Am J Neuroradiol, 2009, vol. 30, pp. 649-661.

* cited by examiner

DEVICES FOR THE REMOVAL OF CLOTS

TECHNOLOGICAL FIELD

The present disclosure relates to anchoring and retrieval of a corpus in an organ of a subject, in particular narrow tubular organs such as small blood vessels.

BACKGROUND ART

References considered to be relevant as background to the presently disclosed subject matter are listed below:
[1] Nogueira et al., *AJNR* 2009, 30, 649-661
[2] Grunwald et al. *The American Journal of Neuroradiology* 2011, 32, 238-243
[3] Mordasini et al. *The eJournal of the European Society of minimally invasive Neurological Therapy*, 2012: 1238000077
[4] U.S. Pat. No. 7,766,921
[5] U.S. Pat. No. 8,715,227
[6] U.S. Pat. No. 6,685,722
[7] WO 2013/054324
[8] Gralla et al., *Am J Neuroradiol* 2006, 27, 1357-1361
[9] WO 2011/130256
[10] Gory et al., *Am J Neuroradiol* 2013, 34, 2192-2198
[11] Levy et al., *Am J Neuroradiol* 2006, 27, 2069-2072
[12] WO 2017/072761

Acknowledgement of the above references herein is not to be inferred as meaning that these are in any way relevant to the patentability of the presently disclosed subject matter.

BACKGROUND

The removal of blood clots and plaque from blood vessels by use of minimally invasive procedures is nowadays a well-established practice. A stroke event associated with a blood clot occurs as a result of disturbance in the blood vessels supplying blood to the brain, leading to sudden death of brain cells. This can be due to ischemia (lack of glucose and oxygen supply) caused by thrombosis (~80% of strokes) or due to a hemorrhage (~20% of strokes). The annual prevalence of stroke is estimated to be 15 million people worldwide and it is one of the leading causes of death (~10% of all deaths) and long-term disability. Furthermore, stroke is one of the most costly health problems in America and the Western world, with estimated direct and indirect costs of $38.6 billion annually. The majority of the damage caused by a stroke is due to secondary stroke damage which threatens the functionally of the impaired region that surrounds the infarct core; the ischemic penumbra. Early medical intervention (for re-canalization) can inhibit this process and reduce the risk for irreversible neurological damage.

The goal of treatment for stroke resulting from thrombus remains the same: safe and rapid re-establishment of oxygenated blood flow to the affected tissue. Guidelines and protocols for the treatment of ischemic stroke are, for example, those published by the American Society of Neurology and the American Society of Neurosurgeons or The European Stroke Organization (ESO). More specifically, the pharmacologic standard of care for ischemic stroke patients to date is by intravenous (IV) tissue plasminogen activator (rt-PA). Improvement in re-canalization rate may be achieved when rt-PA is used intra-arterially (IA) within 6 hours of symptom onset, in patients with occlusions in a large-vessel (e.g. middle cerebral artery), or patients who have contraindications for the use of IV thrombolysis. However, this treatment may increase the risk for intracranial hemorrhage and is currently not approved for use worldwide. Beyond the failure rates of thrombolytic therapy, it is also limited in the time window for treatment and indicated population. Therefore, in patients who have either failed IV rt-PA therapy or who are either ineligible for or have contraindications to IV rt-PA use, or are out of the therapeutic window when medical support can be initiated, neurothrombectomy devices have been used for the re-establishment of blood flow.

Various mechanical approaches to fragment or retrieve clots have been utilized and reported in the clinical literature. These include, inter alia, endovascular (intracranial) thrombectomy, endovascular thromboaspiration, mechanical thrombus disruption and thrombus entrapment devices [1-6]. Intracranial thrombectomy may provide rapid flow restoration with a potentially lower likelihood of clot fragmentation and distal embolism, lessens and even precludes the use of chemical thrombolytics—thus reducing the risk of neurotoxicity and intracranial hemorrhage. By avoiding the use of chemical thrombolytics, it may be possible to extend the treatment window to at least 8 hours. In addition, re-canalization occurs without the disruption of the blood-brain-barrier. For example, some systems are based on deployment of devices in a collapsed state, that are expanded for retrieval of the blood clot once inserted into the blood vessel [4]. Others comprise a plurality of strands, and have contracted and expanded configurations [5-7, 9, 12].

Due to the variability in the properties of blood clots, many of the devices described in the art are suitable for extraction of a specific type of clots. Moreover, in most cases the devices are designed to provide support for the artery as well as function to provide embolic protection, thereby necessitating direct contact with the internal face of the blood vessel. Such contact often causes additional damage to the blood vessel when the device is manipulated and moved within the vessel during the different stages of the procedure. Further, in some configurations, the manner by which the device engages the clot may cause fragmentation of the clot, thus increasing the risk of emboli and necessitating the deployment of additional embolic protection elements/systems. Thus, there is a need for a device allowing extraction of various clots from a variety of blood vessels and reducing the risk of clot disintegration, while providing greater operational flexibility and minimal blood vessel damage.

GENERAL DESCRIPTION

The present disclosure relates to medical devices, systems and methods for capturing, retrieving and/or extracting a corpus located in a tubular organ. Thus, the device of this disclosure is suitable for carrying out various procedures for removal of occlusive corpora from tubular organs. An exemplary procedure may be thrombectomy (i.e. removal of blood clots), typically from narrow blood vessels such as, but not limited to, those existing in the brain, by capturing the corpus within the device in a manner permitting its extraction from the blood vessel without significantly fracturing the corpus or without significantly damaging the blood vessel from which the corpus is extracted.

Thus, this disclosure concerns a medical device that is introduced into a blood vessel by catheterization, having a functional unit at its distal end, that is configured for relatively tight coupling to the blood clot. Through an action, to be described below, which involves relative displacement of two functional segments, referred to below as the proximal segment and the distal segment, the deformation of a corpus-engaging segment of the device causes the formation of a cage-like structure that physically anchors into the clot and captures it.

In the context of the present disclosure, the term corpus encompasses blood clots, plaque, cholesterol layers, thrombus, naturally-occurring foreign bodies (e.g. tissue portions trapped within or adhered to the inner face of the tubular organ), non naturally-occurring foreign bodies (e.g. non-biological objects trapped within, adhered to or penetrating through the tubular organ), and the like.

The term tubular organ means to encompass any anatomical lumen of a subject to be treated that enables flow of a bodily-fluid therethrough. The organ may be a blood vessel (a vain, an artery, micro blood vessels, etc.), or a non-vascular anatomical organ, such as fallopian tubes, urinary tract (e.g. ureter, urethra, kidneys), biliary tract (bile ducts), gastrointestinal tract, airways and any other anatomical lumen in which partial or full blockage may occur.

In one of its aspects, this disclosure provides a medical device for capturing at least one corpus located in tubular organ comprising a guidewire extending along a proximal-distal direction and at least one capturing unit; the capturing unit envelops at least a distal portion of the guidewire, having a proximal segment and a distal segment integrally linked to one another by a deformable clot-engaging segment. At least one of the proximal or distal segments that is displaceable along the guidewire towards the other of the proximal or distal segments, to thereby deform the clot-engaging segment into a deformed state. The clot-engaging segment comprises a plurality of flexible and deformable elongated elements extending between two ends, integral with both the distal and the proximal segments; each of the elongated elements has an integral, apex-forming portion defined in between a proximal portion adjacent the proximal segment and a distal portion adjacent the distal segment, and having a non-deformed state in which the element extends along the guidewire and adjacent thereto, and a deformed state in which the element arches radially away from the guidewire defining a loop with an apex formed by the apex-forming portion. At least one of these elongated elements comprises one more integral spikes that, in the non-deformed state, project from the elongated element in a first direction generally parallel to the guidewire, and that upon deforming the elongated element into the deformed state, switches its orientation such that the spike projects in a second direction different from the first direction.

As noted herein, provided by this disclosure is a medical device having two basic constituents: a guidewire extending along the proximal-distal direction; and a capturing unit. In the present disclosure reference is made to proximal-distal directionality. In the device of the present disclosure, the guidewire extends between a proximal end of the wire, that may be linked to a manipulation device to be described below, and a distal, typically free, leading-end of the wire. The proximal-distal axis is defined as the longitudinal axis extending between the wire's ends. Thus, the terms proximal and distal (or any lingual variation thereof), refer to the position of various elements along the proximal-distal axis. Accordingly, axial displacement is meant to refer to a movement of an element along the axis, whether in the proximal-distal direction or in the distal-proximal direction.

Although the guidewire and its associated capturing unit are not necessarily straight and can extend, in addition to a straight path, in a wavy, curved or other path, for the purpose of description, the term axial will be used to define a direction extending along a section of the guidewire.

The guidewire is typically formed out of a biocompatible material, such as polymeric or metallic biocompatible materials known in the art. Examples of suitable materials include metal, metal alloy, a metal-polymer composite, combinations thereof, and the like, or any other suitable material.

Some examples of suitable metals and metal alloys include stainless steel, 316LV stainless steel; mild steel; nickel-titanium alloy such as linear-elastic and/or super-elastic nitinol; other nickel alloys such as nickel-chromium-molybdenum alloys, nickel-copper alloys, nickel-cobalt-chromium-molybdenum alloys, nickel-molybdenum alloys, other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys; platinum enriched stainless steel; combinations thereof; and the like; or any other suitable material.

In some embodiments, the guidewire is flexible. The guidewire has a diameter which is smaller than the diameter of the tubular organ, i.e. blood vessel, into which the device is inserted. By some embodiments, the diameter of the guidewire is between about 0.0045 inches and 0.018 inches. It is of note that other dimensions are also contemplated.

The capturing unit has a proximal end and a distal end, and extends along the guidewire between the proximal and distal ends. The capturing unit envelops at least a distal portion of segment, referred to herein as the distal segment, which is at the distal-most portion of the capturing unit, and another segment referred to herein as the proximal segment, both of which are integrally linked to one another by a deformable corpus-engaging segment. At least one of the proximal or distal segments are capable of axial displacement along the guidewire toward the other segment, and, through this displacement, the corpus-engaging segment is deformed from its initial, non-deformed state to a deformed corpus-engaging state.

Typically, one of the distal and proximal segments (e.g. the distal segment) is fixed to the guidewire; for example, the end portion of the distal segment may be fused, soldered, glued or otherwise tightly connected to the guidewire. In this way, the displacement of the distal segment is achieved through displacing the guidewire in the proximal direction, i.e. in the direction toward the proximal end thereof.

The corpus-engaging segment comprises a plurality of flexible and deformable elongated elements that extend between the proximal and distal ends of the corpus-engaging segment, and are integral with both the distal and the proximal segments. In the non-deformed state the elongated elements are generally axially orientated. Each of the elongated elements has an integral, apex-forming portion that is defined in between a proximal portion adjacent to the proximal segment and a distal portion adjacent to the distal segment. Upon displacement of one of the distal or proximal segments, the elongated elements reconfigure from their non-deformed state in which, as noted above, they are generally axially orientated, into a deformed state in which the elongated elements arch radially, away from the guidewire, thus defining an arch or a loop with an apex, formed by an apex-forming portion. Namely, by the axial movement of one of the proximal or distal segments, the generally axially oriented elongated elements are deformed into an arch or a loop that extends radially away from the guidewire.

The apex-forming portion may be off-center of the elongated element, and accordingly, the proximal portion and distal portion of the elongated elements may be of non-equal lengths. By some embodiments, this may cause the formation of a loop, defined by the elongated element in its deformed state, to have a general shape resembling that of half of a cardioid, in which the shorter portion (typically the distal portion) has a general opposite orientation to the longer portion.

Such arching forms a rounded configuration once the capturing unit is deformed, assisting in smooth retraction of the deformed units (with the captured corpus) into the catheter. Such smooth retraction also reduces the possible damage to the blood vessel during corpus capturing and retrieval.

It is of note that, in some embodiments, the deformation of the elongated elements from a non-deformed state to a deformed state is reversible; namely, by displacing the guidewire in a direction opposite to the direction used for deforming the capturing unit, the elongated elements may be switched-back from the deformed state to their non-deformed state. This provides the user with the possibility to return the capturing unit to its non-deformed, vessel-introducing state for repositioning and re-capturing attempt with minimal damage to the blood vessel.

According to some embodiments, each capturing unit, independently of the others, may have a length of between about 1 and 10 mm, more typically between 2 and 5 mm. In other embodiments, the capturing units have a non-deformed diameter of between about 0.001 inches (0.0254 mm) and about 0.13 inches (3.302 mm).

Each capturing unit may independently comprise a different number of elongated elements. Thus, in some embodiments, each capturing unit, independently of the others, may comprise between 4 and 12 elongated elements. In other embodiments, each capturing unit in the device consists of the same number of elongated elements.

Each of the capturing units, independently of the others, may be a single layer unit or a multiple-layered unit. Namely, the elongated elements may be arranged in a single layer to form a single layer unit. Alternatively, several layers (typically between 2 and 5 layers) of elongated elements may be stacked to form a multi-layered unit. In the multi-layered unit, the layers may be arranged such that the elongated elements of one layer are parallel to the elongated elements of the subsequent layer. In another arrangement, the layers are arranged such that the elongated elements in at least one layer are off-set to the elongated elements of a subsequent layer. Such multi-layering enables tailored flexibility of the capturing units as well as permits multi-stage deployment of the capturing unit.

In some embodiments, the capturing unit is made of a metal or alloy, e.g. a shape memory metal or alloy (such as nitinol or stainless steel), such that their transition from the non-deformed state to the deformed state is facilitated by the shape-memory properties of the alloy.

Further, when the device includes more than one capturing unit, all of the capturing units may be simultaneously deployed (i.e. transitioned from the non-deformed state to the deformed state), or at least some of the capturing units may be deployed followed by deployment of others of the units. Selective deformation (namely, selective deployment) may be obtained by various means, for example, by controlling the force required to deform the elongated elements—e.g. by varying the thickness of the elongated elements. Namely, the thicker the elongated elements are, the more resistant they are to deformation, and hence a larger force will be required for deformation. Similarly, the elongated elements may be made of materials having different moduli of elasticity, such that for low modulus materials deformation will require application of less force than for elongated elements made of a higher modulus material. In another example, selective deformation of the capturing units may be obtained by forming elongated elements that are angled with respect to the longitudinal axis of the capturing unit (i.e. the elongated elements may be longitudinally tilted with respect to the axis)—the larger the tilting angle, the less force is required for deforming the capturing unit. Further, without wishing to be bound by theory, such an angle functions to ensure arching out of the elongated elements during deformation, as well as dividing the mechanical loads and strains applied on the elongated elements during their deformation and engagement with the corpus in order to minimize the risk of their breakage during deformation.

According to some embodiments, the capturing units are spaced apart along the guidewire by one or more spacers, which may, for example, be constituted by a spacer (e.g. a rigid or flexible tube) of defined length or by sections of the guidewire having larger diameter than the rest of the guidewire.

As noted above, at least one (at times all) of the elongated elements comprises one or more integral spikes. In the non-deformed state, the integral spike projects from the elongated elements in a first generally axial direction. Once the elongated element is deformed, the deformation also causes a change in orientation of the spike from its first generally axial direction to a second direction, different from the first direction, thereby aiding in anchoring into the corpus and capturing thereof.

Spikes in the proximal portion of the elongated element will be referred to herein as proximal spikes; and spikes in the distal portion will be referred to as distal spikes. Typically, at least one of the spikes is a distal spike which, in the non-deformed state points in the direction of the distal segment, and once the elongated element is deformed into the deformed state, the distal spike switches its orientation to point generally in the direction of the proximal segment. A typical example is in the case of a shape that resembles half of a cardioid in the deformed state as described herein.

By another embodiment, the device has at least one proximal spike that changes its orientation from pointing in the direction of the proximal segment in the non-deformed state, to an orientation in which the proximal spike points to another direction, essentially in the direction of the distal segment in the deformed state.

Thus, in addition to the capturing of the corpus by the deformed elongated elements, the change in orientation of the spikes during deformation of the elongated elements will cause at least some of the spikes to be anchored within the corpus, thereby increasing the mechanical engagement between the capturing unit and the corpus. In other words, due to the change in orientation of the spikes as a result of the deformation of the elongated elements, the spikes are anchored into the corpus and facilitate its anchoring to the device to enable its extraction.

In some embodiments, each of the elongated elements is formed with at least one spike. In some other embodiments, each of the elongated elements is formed with at least one proximal spike and at least one distal spike. In additional embodiments, some of the elongated elements are formed with one or more proximal spikes and the rest of the elongated elements are formed with one or more distal spikes.

In use, the device is typically inserted into a blood vessel by a catheterization procedure—using a delivery catheter, and pushed along the blood vessel until its distal portion penetrates through a corpus, e.g. a blood clot, to be removed. The corpus-engaging segment is then deformed by relative displacement of the distal and proximal segments, as described above, to cause the corpus-engaging segment to engage with the corpus and capture it. The device with the captured corpus can then be pulled back through the catheter to thereby remove the corpus from the blood vessel.

In order to assist in monitoring of the capturing and extraction process, at least one of the proximal or distal segments, at times both segments, may comprise an radiopaque marker, e.g. a platinum iridium (Pt—Ir) or gold marker.

Typically, after initial penetration, the device is pushed through the corpus until the corpus-engaging segment comes to be within or distal to the corpus. The deformation of the corpus-engaging segment will then, particularly in the cardioid embodiment described above (namely that where the loop in the deformed state has half a cardioid-like shape), forms a cage-like shape that can efficiently capture the corpus and remove it in a manner described herein.

The device may be inserted into the organ via a catheter, a micro-catheter or an endoscope. In some operational procedures, usually depending on the physical properties of the corpus (i.e. geometry, density, consistency, etc.), a leading bore may be formed in the corpus by a preliminary stage using a designated tool. The leading bore enables subsequent insertion of device, such that at least a part of the capturing unit penetrates beyond the corpus in the distal direction.

In cases where the corpus has suitable consistency, the device itself may be used to form such a leading bore. Namely, where the corpus has a suitable consistency, the leading end of the guidewire may be used to penetrate through the corpus. In such embodiments, the leading end of the guidewire may be tapered, slanted and/or grooved to permit penetration through the corpus. The leading end may be made of the same material as the guidewire or of a different material.

Unlike some of the thrombectomy devices known in the art, the device of this disclosure does not merely forms a net or a mesh that form physical barriers in the blood vessel and by that permits the retrieval of the corpus, but rather the device of this disclosure anchors (i.e. penetrates into) the corpus and captures at least a portion thereof. Further, during deformation of the capturing unit, the corpus is mechanically interlocked (for example by pinching) between the deformed elongated elements, permitting its capturing and retrieval. Thus, and as also explained herein, the device of this disclosure does not need to be dimensioned to encompass the entire-cross section of the organ. This allows for both a relatively small device (having a small volume imprint) when introducing the device into the blood vessel, as well as a relatively small volume imprint of the deployed device. Such small dimensions reduce the risk of possible damaging the blood vessel during the corpus's capturing and retrieval procedure. Further, the geometry of the deployed device minimizes fragmentation and the risk of emboli. Therefore, the presently disclosed devices also provide effective removal of occlusive corpora from a tubular organ while minimizing the risk of injury to the organ's wall during retrieval.

Thus, in some embodiments, the capturing unit is dimensioned to exert a radial force of no more than about 1N (in a conduit having a diameter of 2 mm and when in contact with the internal walls of the conduit) on the internal surface of the organ when in the deformed state.

In some embodiments, the number of capturing units in the device may be between 1 and 10. In other embodiments, the number of capturing units is 1, 2, 3, 4, 5, 6, 7, 8, 9 or 10.

In embodiments where the device comprises at least two capturing units, each of the capturing units may independently comprise a different number of elongated elements. Further, each of the capturing units may, independently of the others, be fixed to the guidewire at either its relative proximal or distal segments.

In some embodiments, each of the capturing units, independent of the others, may have either a short proximal portion and a longer distal portion, or a short distal portion and a longer proximal portion. Thus, in some embodiments, where at least one of the capturing units has a short proximal portion and a longer distal portion and an adjacent capturing unit has a short distal portion and a longer proximal portion, a pair of capturing units is formed, by which a cage-like structure (with the capturing units forming oppositely-oriented half-cardioid loops) that captures the corpus. Such arrangement may further assist in capturing and compacting the corpus once the two oppositely-oriented deformed capturing units proximate one another due to the displacement of the guidewire.

The capturing units, in their deformed state, may define an angle with the guidewire, or be configured to be deformed into a normal radial direction, i.e. projecting radially normally relative to the longitudinal axis defined by the guidewire. In some embodiments, when more than one capturing units are deployed, the distal capturing unit may be deformed into a normal radial direction relative to the guidewire in order to minimize further deformation of the distal unit when retrieved into the catheter.

It is of note that the capturing units may differ in their length, or at least differ in the length of their elongated elements. For example, in a pair of capturing units, the proximal unit may have elongated elements that are longer from those of the distal unit, such that once deformed and pulled closer together by the guidewire, the deformed distal unit has a radial dimension that is smaller than the deformed proximal unit, permitting the distal unit to be partially inserted into the proximal unit. In addition to compactization and caging of the corpus, such an arrangement assists in maintaining the arched portions of the distal unit from contacting the blood vessel during extraction of the device by pulling in the proximal direction.

In other embodiments, all of the capturing units have the same deformed orientation, namely either all having a short proximal portion and a longer distal portion or a short distal portion and a longer proximal portion.

According to some embodiments, the device may further comprise additional functional elements. One such functional element may be in the form of deformable tubes, that have a tubular configuration having a longitudinal axis generally parallel to the guidewire in a non-deformed state, and a deformed state in which they deform into a radial, typically symmetrical, mesh-like structure. Such deformable tubes, once in their deformed state, may prevent drifting of emboli, as well as provide additional anchoring points into the corpus.

In some embodiments, such deformable tubes may be constituted by stranded wires, defining together a tubular structure. In other embodiments, the deformable tubes may be constituted by tubular bodies, having a plurality of parallel longitudinal cut-outs that are defined between a proximal end section and a distal end section of the tubular body.

Such deformable tubes may be used concomitantly with the capturing units to assist in caging the corpus once captured. For example, after deforming a capturing unit into the deformed state and its anchoring into the corpus, a deformable tube may be deployed either distal to and/or proximal to the capturing unit to form a cage-like structure about the corpus.

The deformable tubes may define an angle with the guidewire when in their deformed state, or be configured to be deformed into a normal radial direction, i.e. projecting radially normally relative to the longitudinal axis defined by the guidewire. In their deformed state, the deformable tubes may have a radial dimension which is similar to, larger or smaller than an adjacent capturing unit in its deformed state.

It is further of note that the deformable tube may be an independent element associated with the guidewire. In other embodiments, a deformable tube may be integral with the capturing unit, being distal and/or proximal to the elongated elements. For example, the capturing unit may be made of a metal tube in which elongated elements are defined in one of the proximal or distal portions to constitute the a deformable corpus-engaging segment, while a deformable tube (or a braided tube) is defined in another portion of the capturing unit and being integrally formed from the same metal tube. In such an arrangement, the deformable corpus-engaging segment and the deformable tube are typically designed to require different deformation forces, as to enable deformation in a desired sequence for capturing the corpus.

Other additional functional elements may be used to further reduce in the risk of embolization of the thrombotic material during endovascular recanalization procedures may be obtained by inclusion of one or more embolic protection elements. Thus, in some embodiments, the device may further comprise at least one embolic protection element, which may be positioned proximal and/or distal ends of the capturing unit.

One non-limiting example of such embolic protection elements includes an occlusion balloon, displaceable over a wire proximal to the thrombus in order to trap and aspirate thrombotic debris released during the thrombectomy procedure. Another non-limiting example may be a filter displaceable over a wire distal to the thrombus, permitting trapping and aspiration (or capture and retrieve) of thrombotic debris released during the thrombectomy procedure.

In another embodiment, the embolic protection element may be a protective sleeve that forms a closed or partially-closed cover surrounding the thrombus during retrieval. In another embodiment, the cover may further provide protection and support to the vessel wall, reducing the risk of vessel wall injury during retrieval. The cover may have a fixed section at the proximal end of the capturing unit, and a free section extending in a proximal direction. The cover may have a diameter equal or greater that the capturing unit. There may be friction between the cover and the vessel wall resisting proximal movement of the cover, causing the cover to avert over the capturing unit, permitting the free section of the cover to be distal to the capturing zone. Averting refers to inside-out turning of the cover due to movement of the capturing unit within the cover, causing the cover sleeve to protects and cover the capturing unit.

In some embodiments, the embolic protection element may be expandable through self-expanding configurations, or via actuated expansion (e.g., a shape memory alloy, spring expansion, or other actuation), or any other suitable mechanism known in the art Similar to the elements of the capturing unit, the embolic protection element(s) may include radiopaque markers, such as gold and platinum for improved visibility under fluoroscopic imaging. The embolic protection element may be made of any suitable material known in the art, for example, biocompatible polymer sheet, biocompatible metal or alloy, etc.

It is of note that at least one, optionally at least some, or even all of the elements of the device (i.e. the guidewire, the capturing unit, the embolic protection element, and/or any other element being part of the device), as well as elements of the system which are inserted and/or come into contact with bodily tissues, may be coated by a suitable biocompatible coating. For example, a polymeric coating, a hydrophilic coating, etc.

Although some specific examples are provided above with respect to the materials from which the different device parts may be made of, it is noted that such examples are non-limiting. Namely, the different parts of the device may independently comprise metals, polymers, ceramic materials; may comprise non-bioabsorbable and/or bioabsorbable materials; some or all of the elements coming into contact with bodily tissues may elute desired substances over time (such as drugs, biologics, anti-thrombotics, coagulants, anti-coagulants, anti-inflammatory drugs, thrombolytic drugs, anti-proliferative drugs, healing promotors, re-endothelialization promoters, or others).

In another aspect, the present disclosure provides a medical system for capturing at least one corpus located in tubular organ, the system comprising a handling and manipulation apparatus (HMA) and a device as herein described operable thereby, the HMA being configured for manipulating the device into engagement with said corpus. Once in proximity to the corpus, the device is manipulated into operation by the HMA.

The HMA is configured to axially (and/or rotationally) displace the guidewire, such that the capturing unit is brought into proximity with the corpus. Once in such proximity, the capturing unit is operated (i.e. deployed) by axial displacement of the guidewire induced by the HMA.

The handling and manipulation apparatus (HMA) may comprise an actuator associated with a shaft pipe. As used herein the term shaft pipe denotes an elongated, typically tubular, element, which may be made of any material that can withstand or resist compression loads along the longitudinal axis, for example stainless steel. The shaft pipe typically has a longitudinal lumen, through which the guidewire is threaded. The shaft pipe may be fixedly coupled at its proximal end to the actuator via a shaft pipe handle, and at its distal end to one or more of the cylindrical bodies. The shaft handle on the actuator allows pushing or rotation of the shaft tube, thereby affecting the deformation of the capturing unit.

The HMA is configured to associate with the guidewire of the device, such that the capturing unit is operable by the HMA. The term operable denotes the manipulation of the capturing unit into engagement with the corpus in the conduit, axial movement of the guidewire (and hence deformation of the capturing unit at a desired sequence for anchoring into the corpus), and extracting the corpus.

Thus, the actuator may be used to operate the capturing unit for capturing, anchoring and retrieval of a corpus disposed in the tubular organ. As the capturing units of this disclosure are deformable, the actuator may also be used to shift a deformed capturing unit back into a non-deformed state, for example, when re-trying to capture a corpus after a failed capturing attempt. In an exemplary embodiment, the actuator may comprise two types of handles: a guidewire handle that is fixedly coupled to the proximal end of the guidewire, and a shaft pipe handle that is fixedly coupled to the shaft pipe of the HMA. Applying variable torque onto the different elements mounted onto the guidewire is also contemplated and within the scope of the present disclosure.

The system of this disclosure may be provided as a unitary system. Namely, in another aspect, this disclosure provides a kit comprising a system as described herein and instructions for use.

Alternatively, the HMA and the device may be provided separately, and the practitioner associates between the HMA and the device prior to utilization. Such separation enables replacement of the device at will, while utilizing a single HMA. Thus, in an aspect, the disclosure provides a kit comprising a handling and manipulation apparatus (HMA), at least one device as described herein, and instructions for assembly and/or use.

Further, the device may also be provided as separate element for self-assembly, enabling variance in the amount of operable elements and/or their sequence along the guidewire. Thus, in another aspect, this disclosure provides a kit for assembly of the system as herein described, comprising a handling and manipulation apparatus (HMA); at least one guidewire; a plurality of capturing units; instructions for assembly; and optionally comprising a plurality of spacers.

In some embodiments, the kit further comprises means for associating the guidewire with (i) the HMA, (ii) the capturing units, and/or (iii) the spacers (if such are used).

Another aspect of this disclosure provides a method for removal of a corpus located in a tubular organ, comprising:

(a) introducing a device as described herein into the tubular anatomical organ, such that the capturing unit is brought into proximity with the corpus;

(b) axially displacing the guidewire wire to axially displace at least one of the proximal or distal segments towards the other of the proximal or distal segments, thereby deforming the deformable corpus-engaging segment extending therebetween, such that the plurality of flexible and deformable elongated elements composing the corpus-engaging segment deform from a non-deformed state in which the elements extend along the guidewire and adjacent thereto, into a deformed state in which the elements arch radially away from the guidewire defining a loop with an apex formed by an apex-forming portion, and such that at least one spike formed onto at least one of said elongated elements switches from the non-deformed state in which it project from the elongated element in a first direction generally parallel to the guidewire, to the deformed state in which the spike projects in a second direction different from the first direction, to thereby capture the corpus and anchor the capturing unit therein; and (c) removing the captured corpus from the organ by manipulating the device out of the organ.

Another aspect provides a device or a system as described herein for use in removing a corpus from an anatomical conduit.

As used herein, the term "about" is meant to encompass deviation of ±10% from the specifically mentioned value of a parameter, such as length, diameter, force, etc.

Whenever a numerical range is indicated herein, it is meant to include any cited numeral (fractional or integral) within the indicated range. The term "between" or "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. It should be noted that the range is given as such merely for convenience and brevity and should not be construed as an inflexible limitation on the scope of the invention. Accordingly, the description of a range should be considered to have specifically disclosed all the possible sub-ranges as well as individual numerical values within that range.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

As described above, the system of this disclosure includes a handling and manipulation apparatus (HMA) and a device operable thereby. The device is typically inserted into the vessel to be treated in a non-deformed (non-deployed) state via a pre-inserted catheter or micro-catheter. Once reaching the corpus to be extracted, the corpus capturing unit is deformed (deployed) for capturing and anchoring into the corpus, to enable its extraction from the vessel.

Figure 1:
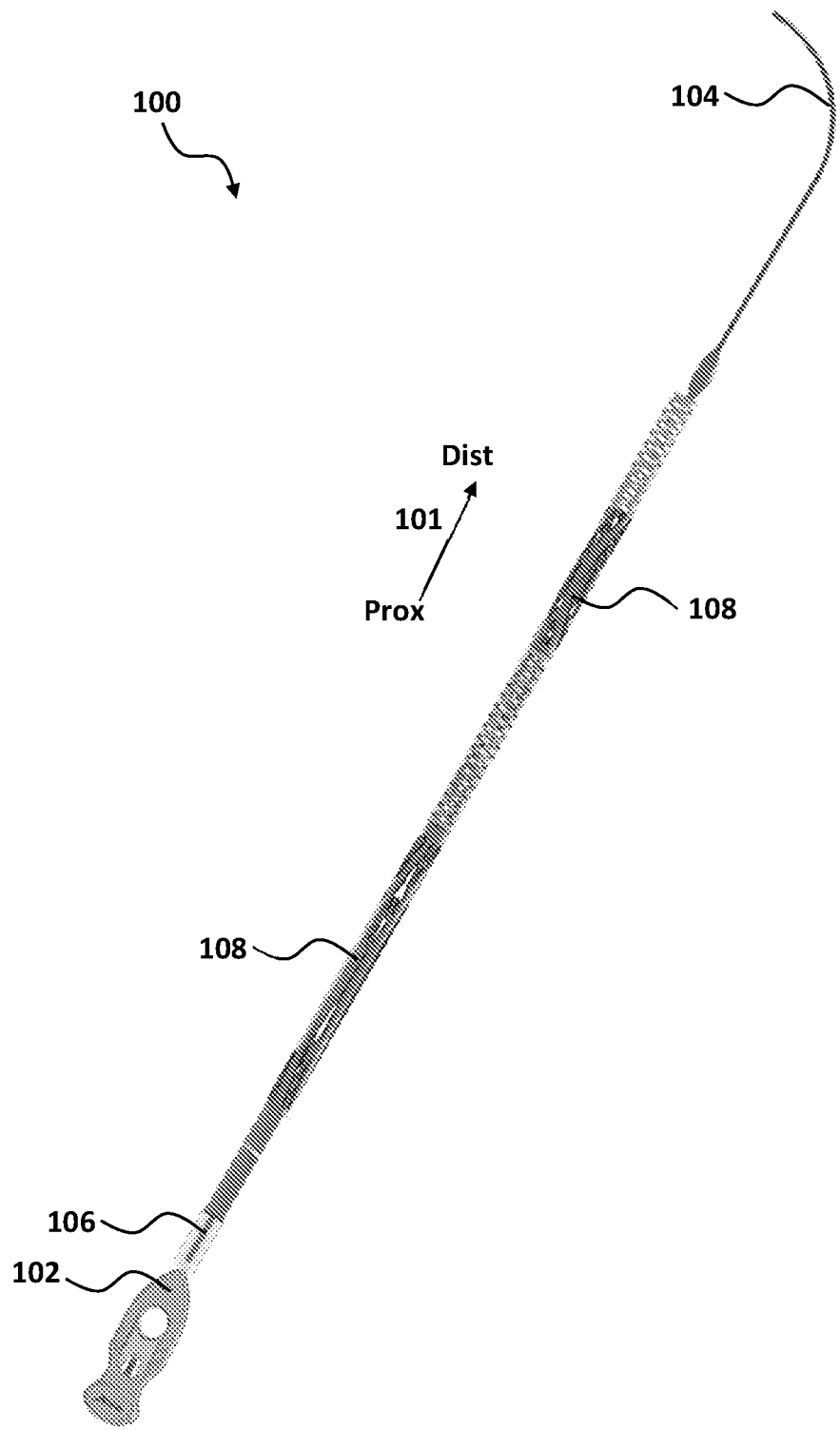
FIG. 1 is a schematic illustration of a system according to an embodiment of this disclosure.

A device 100, shown in FIG. 1, is a generally elongated device extending in a generally proximal to distal direction (noted by arrow 101), from handling and manipulation apparatus 102 to a distal end 104. The device includes guidewire 106, a plurality of capturing units 108, each enveloping a distal portion of the guidewire. It should be noted that in other embodiments, the capturing unit can extend to envelop the guidewire substantially along its entire length. It is also of note that the HMA may have various designs (not shown), and the functionality of the HMA is not limited by any specific external design.

Figure 2:
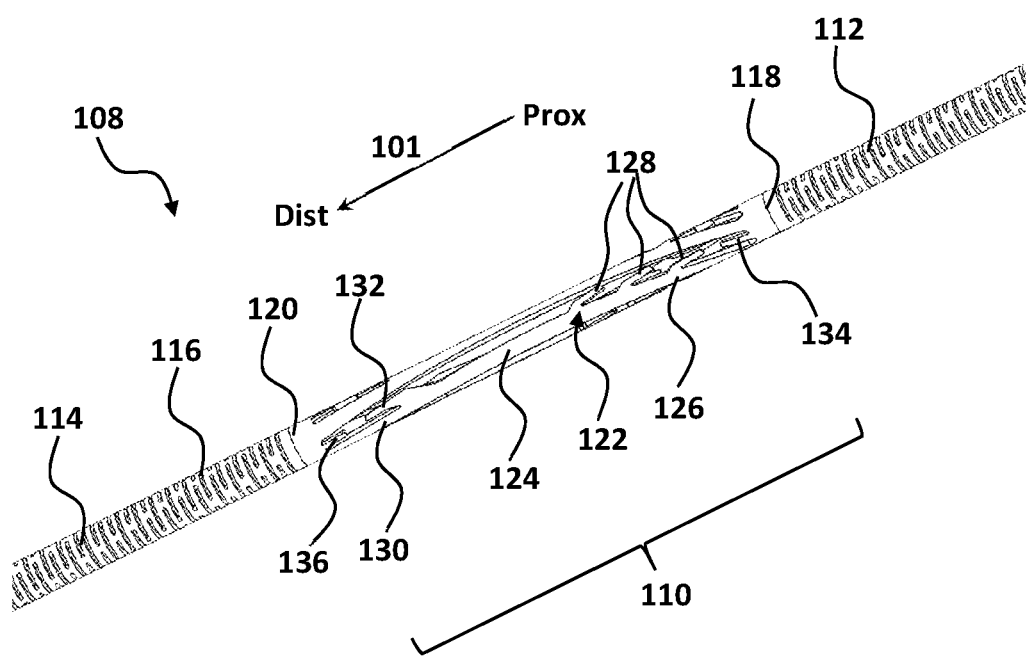
FIG. 2 shows an enlarged view of the capturing unit of the device.

The device includes a corpus-engaging segment 110 separating between proximal segment 112 and distal segment 114 (best seen in FIG. 2). Where the proximal segment does not extend the entire length of the guidewire, the device may also include a stopper (not shown) that may be fixed in position by the delivery catheter that serves to arrest displacement of the proximal segment, upon axial displacement of the distal segment, to induce deformation of the corpus-engaging segment, in the manner to be described below.

The proximal and distal segment of the capturing unit have radial slots 116 intended to impart flexibility to these two segments.

In some embodiments, the distal and proximal segments are integrally formed with the corpus-engaging segment; however, this may not necessarily be the case and by another embodiment they are individual segments associated into one capturing unit once assembled on the wire; and by some other embodiments, such independent segments may be glued or soldered to one another. In the specifically shown embodiment, these three segments are independent segments joined to one another at joints 118, 120.

The corpus-engaging segment has a plurality of flexible and deformable elongated elements 122, generally axially orientated along the proximal-distal axis defined by the guidewire (generally parallel to direction 101). It is noted that that term generally axially orientated does not mean to refer to parallel orientation in the geometric sense, but rather refers to the overall orientation; particularly as can be seen in FIG. 2, the elongated elements have a generally curved orientation, however still following the direction of the guidewire. The elongated elements 122 have each an integral apex-forming portion 124 that is defined, in this example, by a slight narrowing. It is of note that other configurations may be used, such as an apex-forming portion having a smaller thickness or otherwise more flexible than the proximal and distal portions of the elongated element. Once deformed, in the manner to be described below, the elongated element bends about the apex-forming portion which thereby defines the apex of the arched or looped elongated element at its deformed state.

Formed on a proximal portion 126 of the elongated element are proximal spikes 128 (3 such spikes in this specific embodiment) and formed on a distal portion 130 is distal spike 132. The proximal spikes 128 and the distal spike 132 point generally in proximal and distal directions, respectively. In addition, the device of this specific embodiment has at least one proximal and distal base spikes (134, 136 respectively), which further assist in capturing and anchoring the clot.

Figure 3A:
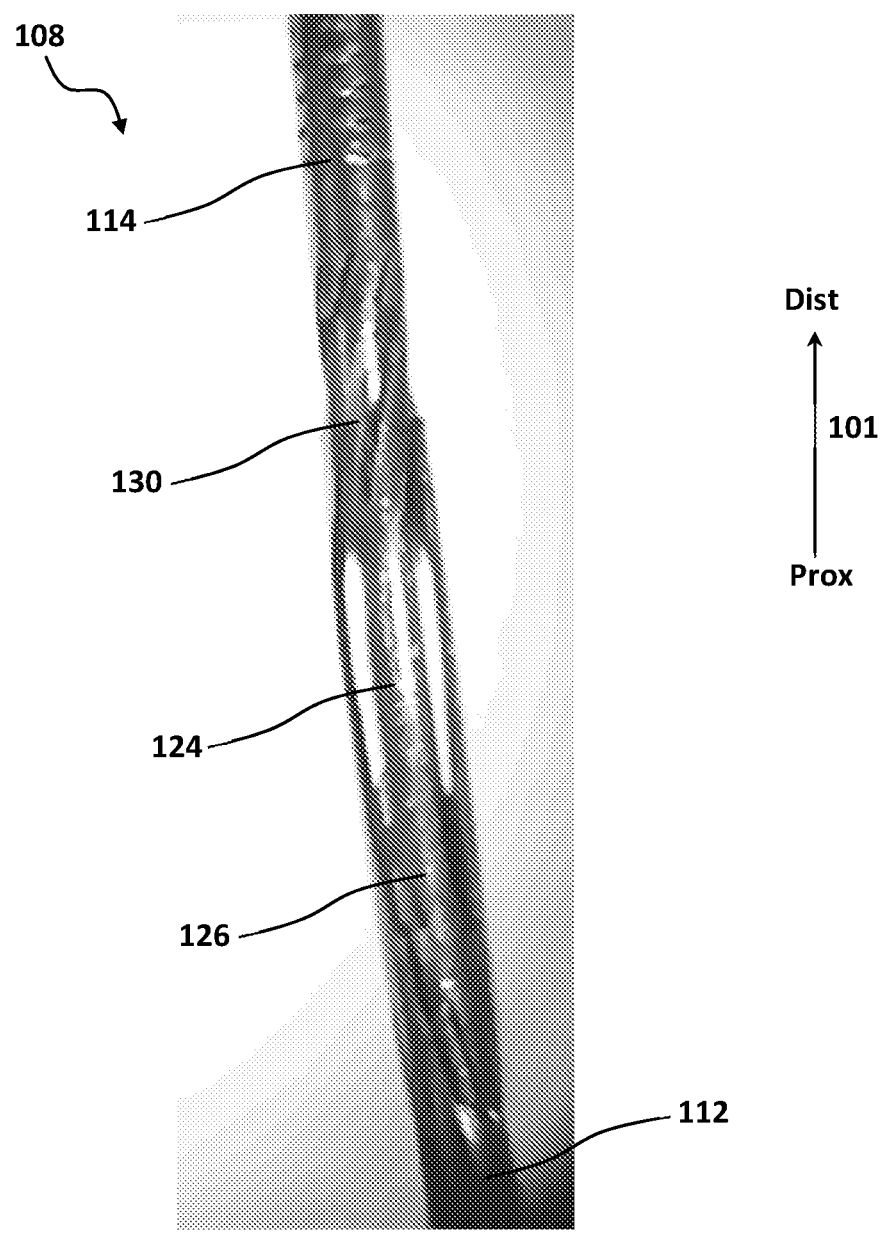
FIGS. 3A-3G are successive sequences from a non-deformed to a fully deformed corpus-engaging state of the capturing unit.
Figure 3B:
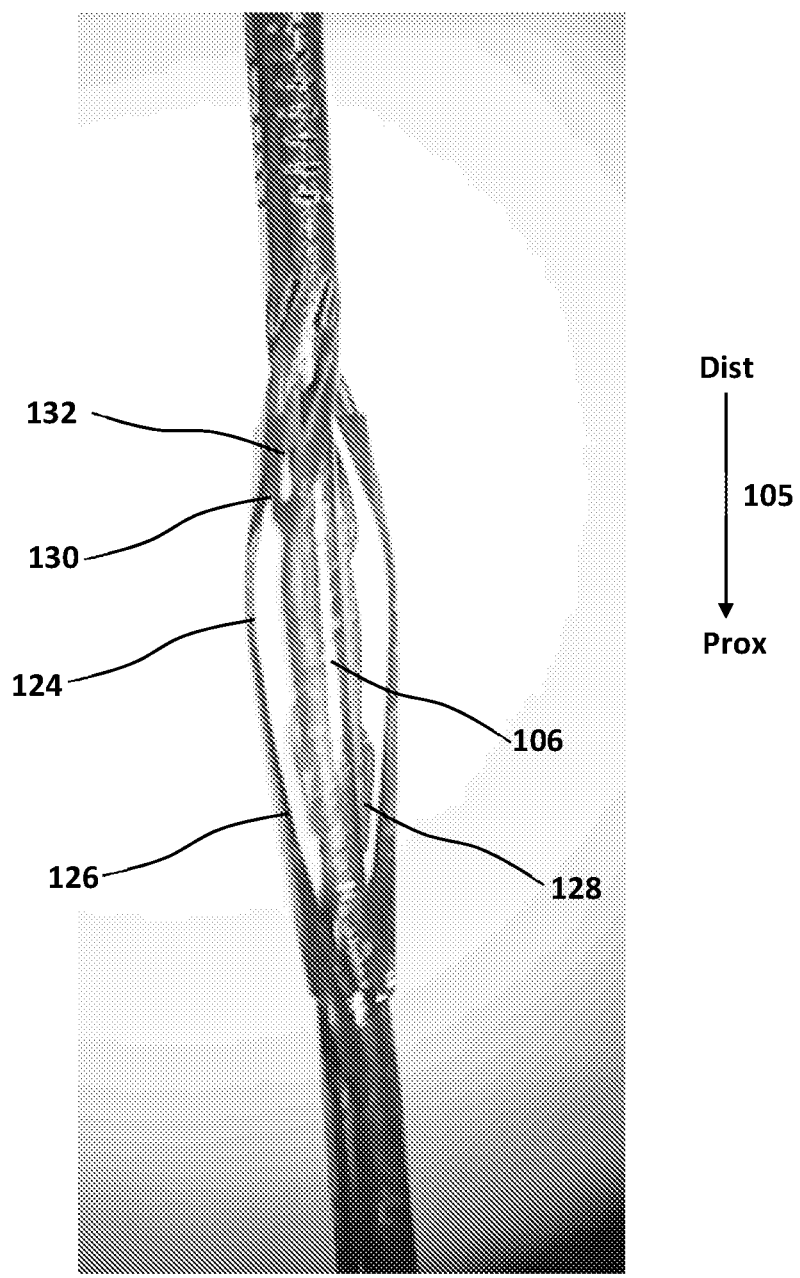
Figure 3C:
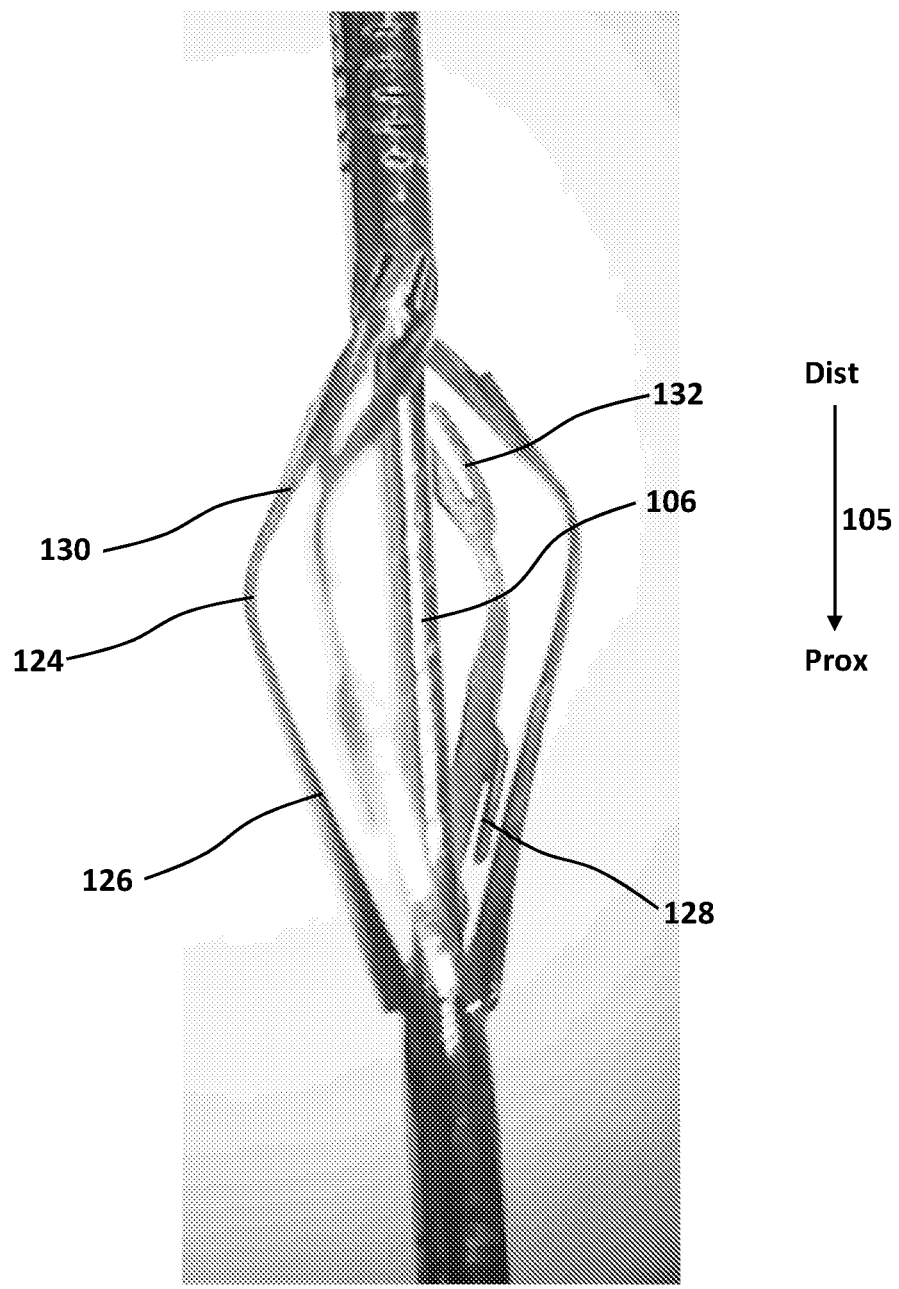
Figure 3D:
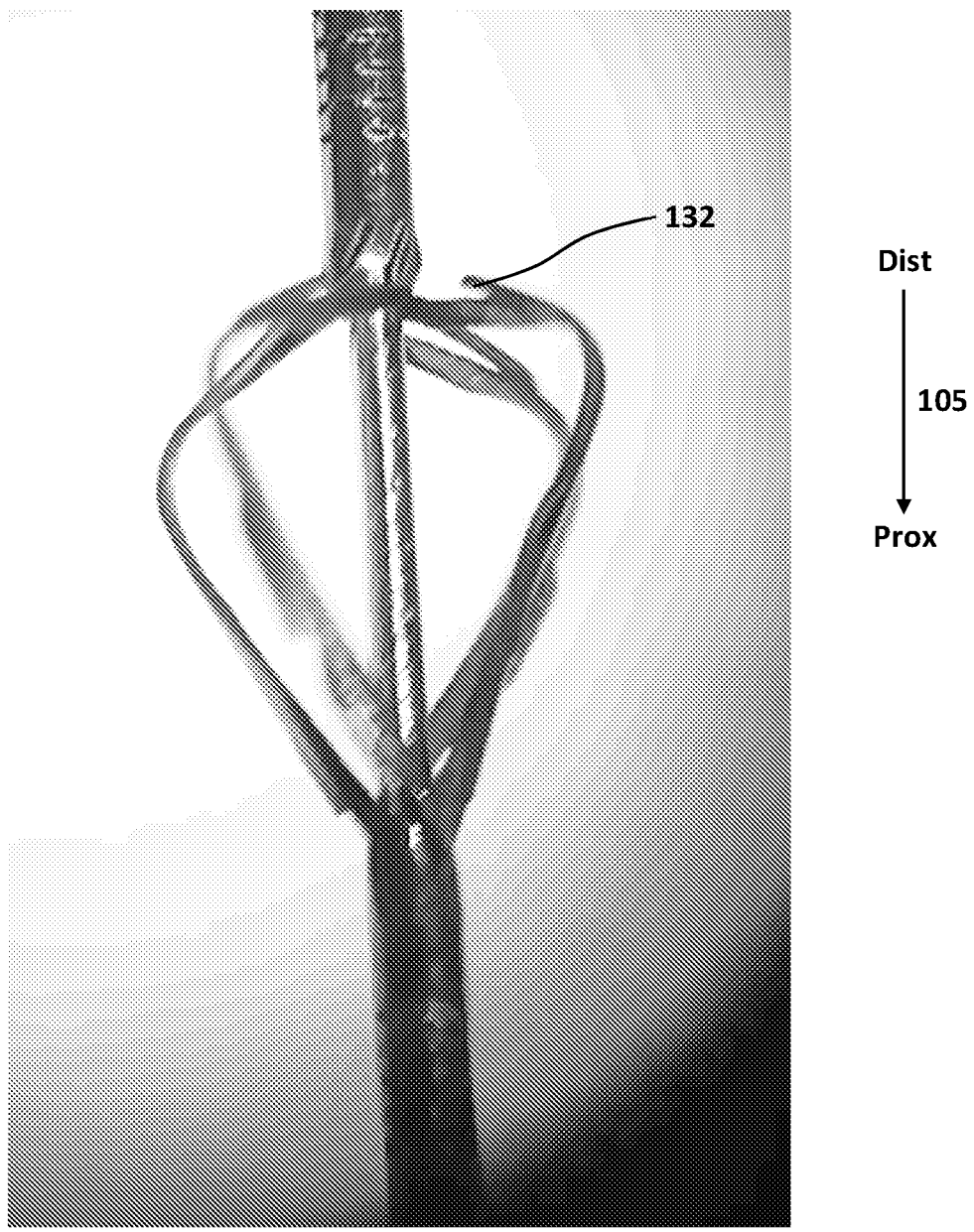
Figure 3E:
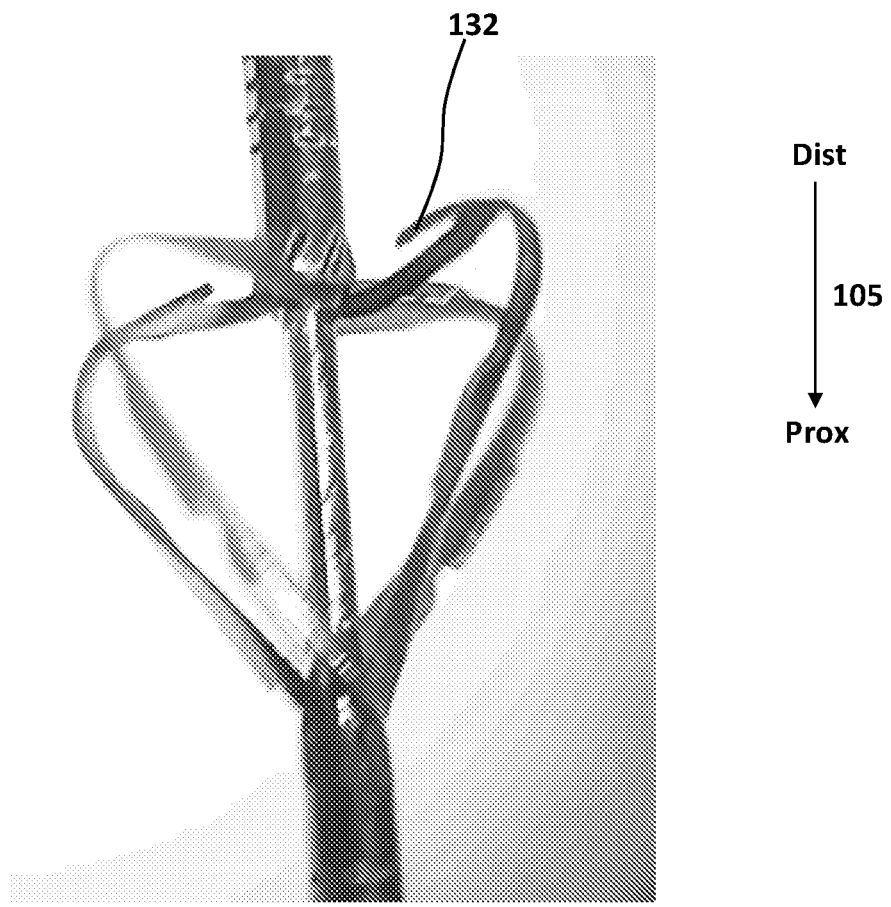
Figure 3F:
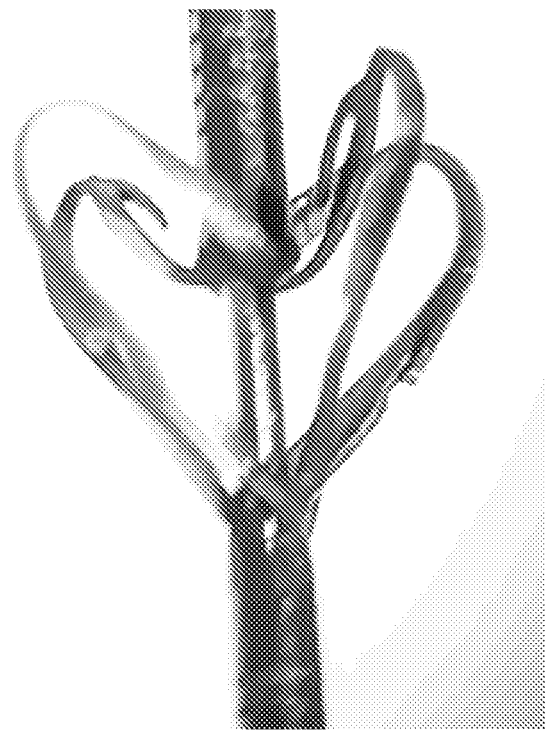
Figure 3G:
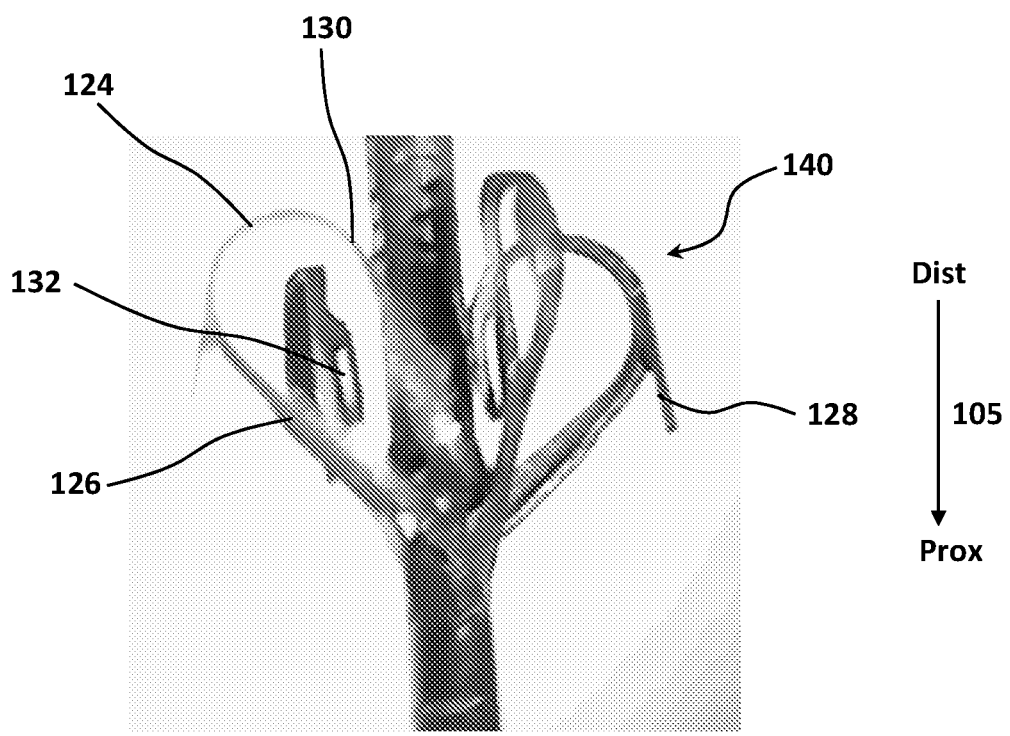

FIGS. 3A-3G show several steps in the deformation sequence from the non-deformed state shown in FIG. 3A to the fully deformed state shown in FIG. 3G. In this specific embodiment, the end of the guidewire 106 is fixed to the end of the distal segment 114 and consequently when the guidewire is pulled axially, in the proximal direction (i.e. toward the proximal end in the direction of arrow 105), it causes displacement of the distal segment 114 in relation to the proximal segment 112 to consequently deform the elongated elements 122.

As can be seen in FIGS. 3B-3G, the elongated elements may be angled with respect to longitudinal axis (i.e. longitudinally tilted with respect to the axis), such that the displacement causes deformation and arching out of the elongated elements, causing the elongated elements to bend about the apex-forming portion 124; the apex-forming portion thus defines the apex of the radially projecting arch or loop. In this deformation process, the elongated elements are deformed into half of a cardioid shape, in which the distal portion 130 assumes a generally opposite orientation from the apex, as opposed to its orientation in the non-deformed state. Consequently, the distal spike 132, which originally pointed in the distal direction, come to point after deformation in the opposite, proximal direction. Such arched structure prevents tangling of the elongated elements during deformation; as well as divides the mechanical loads and strains applied on the elongated elements during their deformation and engagement with the corpus, thus minimizing the risk of their breakage during deformation.

Figure 4:
FIG. 4 shows a device having a plurality of capturing units in their deformed state (two can be seen in this Figure), after their anchoring within a simulating blood clot.

This entire deformation is done in the proximity of the corpus (e.g. a blood clot), causing formation of a cage that tightly holds the corpus for its extraction, as demonstrated in FIG. 4.

As a man of the art may appreciate, although deployment of the device is the examples described herein is exemplified by pulling onto the guidewire (i.e. displacing the wire to the proximal direction), deployment by pushing is also contemplated under similar linear movement and transition of force principles. Further, deformation by rotational movement of the guidewire, i.e. applying variable torque onto the different elements mounted onto the guidewire is also contemplated and within the scope of the present disclosure.

As noted, in addition to the device may further comprise additional functional elements. Some of these elements may be in the form of deformable tubes, that deform to provide a radial, typically symmetrical, mesh-like structure. Such deformable tubes, once in their deformed state, may prevent drifting of emboli, as well as provide additional anchoring points into the clot.

Figure 5A:
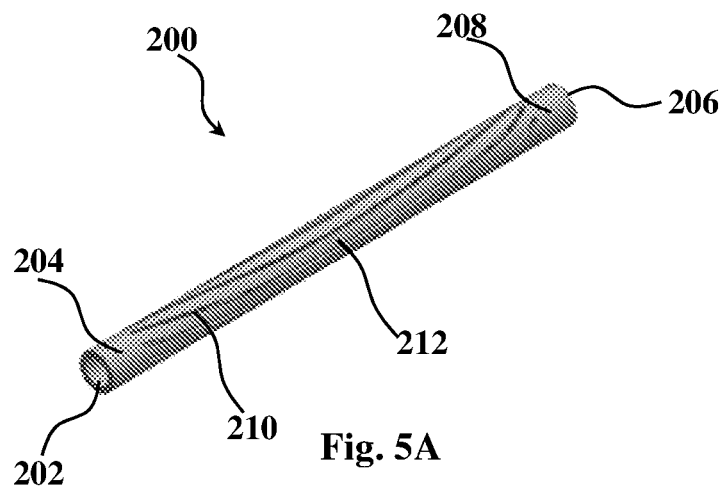
FIGS. 5A-5C are schematic representations of a tube in which the plurality of threads are engaged with one another at and integrally formed with both of the element's ends—side views of a non-deployed state (FIG. 5A) and a deployed state (FIG. 5B) and a front view of the deployed state (FIG. 5C).
Figure 5B:
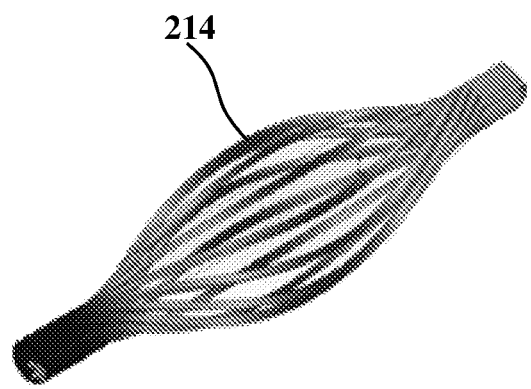
Figure 5C:
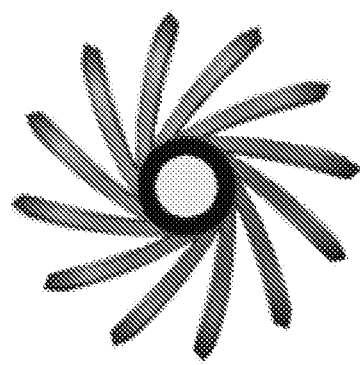
Figure 6A:
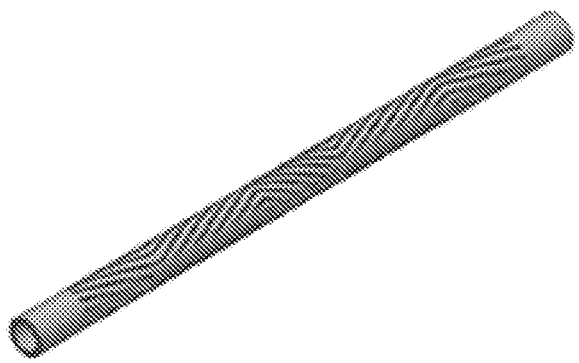
FIGS. 6A-6C are schematic representations of another tube in which the plurality of threads are engaged with one another at and integrally formed with both of the element's ends, having different cut-out geometry for defining the threads—side views of a non-deployed state (FIG. 6A) and a deployed state (FIG. 6B) and a front view of the deployed state (FIG. 6C).
Figure 6B:
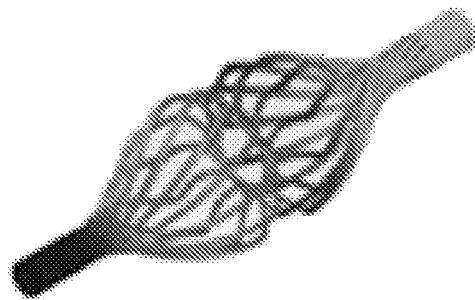
Figure 6C:
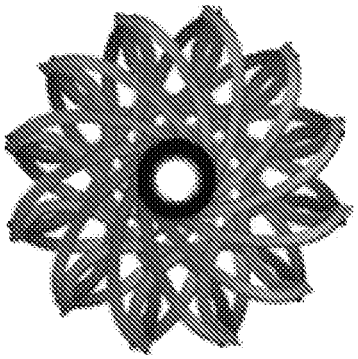
Figure 7A:
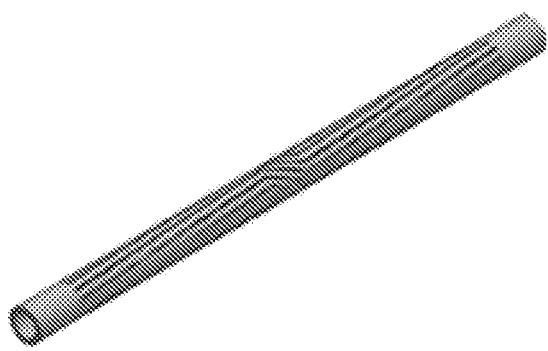
FIGS. 7A-7C are schematic representations of a further tube in which the plurality of threads are engaged with one another at and integrally formed with both of the element's ends, having different cut-out geometry for defining the threads—side views of a non-deployed state (FIG. 7A) and a deployed state (FIG. 7B) and a front view of the deployed state (FIG. 7C).
Figure 7B:
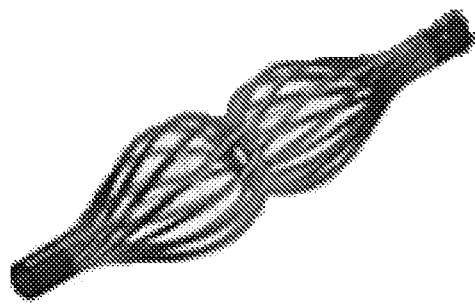
Figure 7C:
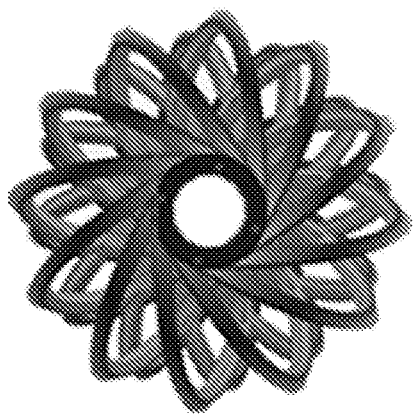

Examples of such deformable tubes are shown in FIGS. 5A-7C. In FIGS. 5A-5C, a tube 200 is schematically represented. As can be seen in FIG. 5A, which demonstrated the non-deformed state of the deformable tube of this example, the tube 200 has proximal end 202 comprising a proximal end section 204, and a distal end 206 comprising a distal end section 208 of the tube. A plurality of parallel longitudinal cut-outs 210 are defined between the end sections 204, 208, such that a plurality of threads 212 are formed, each thread 212 being defined between two adjacent parallel cut-outs 210 and integral with the end sections 204, 208. One of the proximal or distal ends of the deformable tube are associated with the guidewire, and hence once the guidewire is axially displaced in the appropriate direction, the end sections of the deformable tube are brought into proximity to one another, causing the wires to deform and deploy, thereby forming apexes 214, as seen in FIGS. 5B-5C. In this example, the cut-outs 210 are slightly curved, thereby causing a torsional movement of the apexes to enable anchoring of the apexes into the corpus.

Other cut-out geometries are shown in FIGS. 6A-7C, in which the cut-outs are configured to form segmented threads. As can be seen from these figures, cut-outs with varying angles with respect to the longitudinal axis of the deformable tube may be designed to form a variety of mesh-like structures once the deformable tube is deformed.

Figure 8A:
FIGS. 8A-8C show various combinations of a capturing unit with stranded tubes (which may be made of strands, braids or mesh).
Figure 8B:
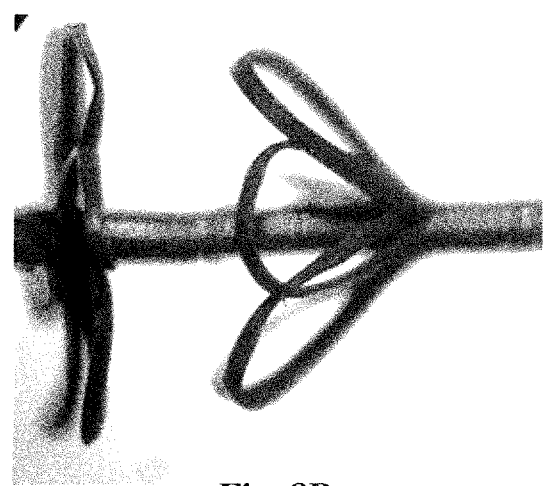
Figure 8C:
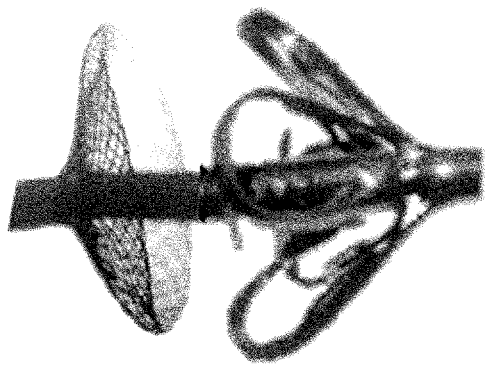
Figure 9A:
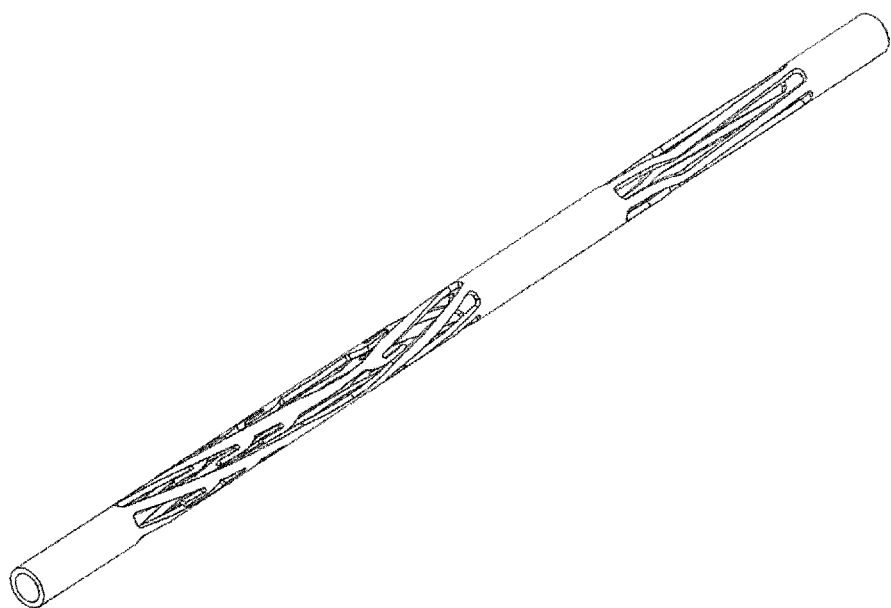
FIGS. 9A-9B show a capturing unit according to an embodiment of this disclosure that is integral with a stranded tube in a non-deformed and deformed states, respectively.
Figure 9B:
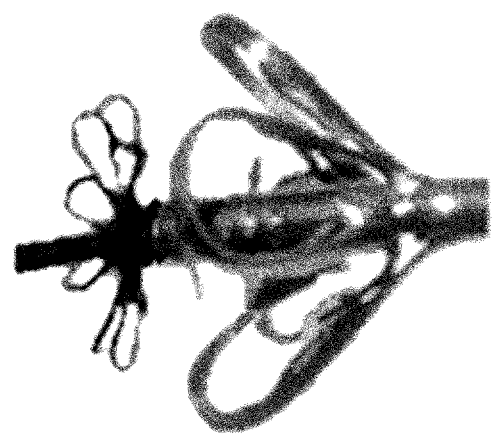

As seen in FIGS. 8A-8C, various combinations of capturing units and deformable tubes may be used to form cage-like structures for caging and capturing the corpus. A specific example is shown in FIGS. 9A-9B, which show an integral capturing unit that comprises a first segment being the deformable corpus-engaging segment and a second segment constituting the deformable tube. Once switched from the non-deformed state (shown in FIG. 9A) to the deformed state (shown in FIG. 9B), the elongated elements in the deformable corpus-engaging segment arch outwards to define a radial angle with the guidewire, while the deformable tube is deformed to a structure which is radially normal to the guidewire. As can also be seen, due to the variance in length of the segments, the deformable tube has a radial dimension which is smaller than the radial dimension of the deformable corpus-engaging segment in their deformed states, such that the smaller deformed segment may be at least partially inserted into the larger deformed segment when the segments are brought closer to one another by pulling on the guidewire. This permits formation of a compact arrangement that assists in compactization and capturing of the clot, while reducing the overall signature of the deformed unit, such that minimal damage is caused to the blood vessel during retrieval of the clot.

The invention claimed is:

1. A medical device for capturing at least one corpus located in tubular organ comprising a guidewire extending along a proximal-distal direction and at least one capturing unit;

the capturing unit
envelops at least a distal portion of the guidewire,
having a proximal segment and a distal segment integrally linked to one another by a deformable corpus-engaging segment, and
at least one of the proximal or distal segments displaceable along the guidewire towards the other segment to thereby deform the corpus-engaging segment into a deformed state;
the corpus-engaging segment comprising a plurality of flexible and deformable elongated elements extending between two ends, integral with both the distal and the proximal segments, the elongated elements, each having
an integral, apex-forming portion in between a proximal portion adjacent the proximal segment and a distal portion adjacent the distal segment,
a non-deformed state in which the element extends along the guidewire and adjacent thereto, and having
a deformed state in which the element arches radially away from the guidewire defining a loop with an apex formed by the apex-forming portion;
at least one of said elongated elements comprising at least one distal integral spike formed at the distal segment such that in the non-deformed state, the at least one distal spike projects from the elongated element and points in a general direction of the distal segment generally parallel to the guidewire, and upon deforming the elongated element into the deformed state, the at least one distal spike switches its orientation such that the at least one distal spike projects and points in the general direction of the proximal segment.

2. The device of claim 1, comprising at least one proximal spike formed at the proximal portion,
in the non-deformed state the at least one proximal spike points in the general direction of the proximal segment, and
in the deformed state the at least one proximal spike points in the general direction of the distal segment.

3. The device of claim 2, wherein one of the distal or proximal portions is shorter than the other.

4. The device of claim 3, wherein in the deformed state, the loop has a general shape resembling that of half of a cardioid, with the shorter portion having a general opposite orientation than the longer portion, and the at least one spike formed on the shorter segment is oriented in a general direction opposite to its orientation at the non-deformed state.

5. The device of claim 1, wherein at least one of the elongated elements comprises at least one proximal spike and at least one distal spike.

6. The device of claim 1, wherein the displaceable segment is the distal segment.

7. The device of claim 6, wherein the distal segment is fixed to the guidewire and the displacement of the distal segment is achieved through displacing the wire in the proximal direction.

8. The device of claim 1, wherein said capturing unit is made of a metal, a shape-memory metal or alloys thereof.

9. The device of claim 1, wherein the capturing unit is configured to exert a radial force of no more than 1N on an internal surface of the tubular organ at the deformed state, when the organ comprises a conduit having a diameter of 2 mm.

10. The device of claim 1, comprising at least two capturing units, spaced apart by a spacer.

11. The device of claim 1, further comprising at least one deformable tube, having a tubular configuration with a longitudinal axis generally parallel to the guidewire in a non-deformed state, and a radial, typically symmetrical, mesh-like structure in a deformed state.

12. The device of claim 1, wherein at least one of the proximal segment and the distal segment comprises an radiopaque marker.

13. The device of claim 1, wherein the tubular organ is selected from a blood vessel, fallopian tubes, urinary tract, ureter, urethra, biliary tract, bile ducts, gastrointestinal tract, airways and any other anatomical lumen.

14. The device of claim 1, wherein the capturing unit comprise a substance to be eluted over time.

15. The device of claim 1, further comprising at least one embolic protection element.

16. The device of claim 15, wherein said embolic protection element being positioned either proximal or distal to the capturing unit along the guidewire, and/or being displaceable along the guidewire to cover the capturing unit.

17. The device of claim 16, wherein said embolic protection element is selected from the group consisting of an avertable sheet and an occlusion balloon.

18. A medical system for capturing at least one corpus located in tubular organ, the system comprising a handling and manipulation apparatus (HMA) and a device according to claim 1 operable thereby, the HMA being configured for manipulating the device into engagement with said corpus.

19. A kit comprising the system of claim 18 and instructions for use.

20. A medical device for capturing at least one corpus located in tubular organ comprising a guidewire extending along a proximal-distal direction and at least one capturing unit;
the capturing unit
envelops at least a distal portion of the guidewire,
having a proximal segment and a distal segment integrally linked to one another by a deformable corpus-engaging segment, and at least one of the proximal or distal segments displaceable along the guidewire towards the other segment to thereby deform the corpus-engaging segment into a deformed state;

the corpus-engaging segment comprising a plurality of flexible and deformable elongated elements extending between two ends, integral with both the distal and the proximal segments, the elongated elements, each having an integral, apex-forming portion in between a proximal portion adjacent the proximal segment and a distal portion adjacent the distal segment, a non-deformed state in which the element extends along the guidewire and adjacent thereto, and having a deformed state in which the element arches radially away from the guidewire defining a loop with an apex formed by the apex-forming portion;

at least one of said elongated elements comprising at least one integral spike that in the non-deformed state project from the elongated element in a first direction generally parallel to the guidewire, and that upon deforming the elongated element into the deformed state, switches its orientation such that the spike projects in a second direction different from the first direction;

the at least one integral spike comprising at least one proximal spike formed at the proximal portion, in the non-deformed state the at least one proximal spike points in the general direction of the proximal segment, and in the deformed state the at least one proximal spike points in the general direction of the distal segment.

* * * * *